United States Patent
Li et al.

(10) Patent No.: US 8,242,286 B2
(45) Date of Patent: Aug. 14, 2012

(54) PHENOXY-PYRROLIDINE DERIVATIVE AND ITS USE AND COMPOSITIONS

(75) Inventors: Jin Li, Pawcatuck, CT (US); Nicole Lee Kolosko, Groton, CT (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 30 days.

(21) Appl. No.: 12/670,010

(22) PCT Filed: Jul. 28, 2008

(86) PCT No.: PCT/IB2008/002028
§ 371 (c)(1),
(2), (4) Date: May 17, 2010

(87) PCT Pub. No.: WO2009/019566
PCT Pub. Date: Feb. 12, 2009

(65) Prior Publication Data
US 2010/0247471 A1    Sep. 30, 2010

Related U.S. Application Data

(60) Provisional application No. 60/954,593, filed on Aug. 8, 2007.

(51) Int. Cl.
*C07D 295/04* (2006.01)
*A61K 31/40* (2006.01)
(52) U.S. Cl. ........................................ 548/540; 514/423
(58) Field of Classification Search .................. 548/540; 514/423
See application file for complete search history.

(56) References Cited

U.S. PATENT DOCUMENTS
7,754,745 B2 *   7/2010   Li et al. .................... 514/363

FOREIGN PATENT DOCUMENTS
GB          1030309          5/1966
WO       WO2007/009236       1/2007

* cited by examiner

*Primary Examiner* — Robert Havlin
(74) *Attorney, Agent, or Firm* — Len S. Smith; Matthew S. Bodenstein

(57) ABSTRACT

The present invention is directed to the compound 2-(4-(hydroxymethyl)phenoxy)-1-(3-(2-(trifluoromethyl)phenoxy)pyrrolidin-1-yl)ethanone, its use as an inhibitor of stearoyl CoA desaturase and to pharmaceutical compositions containing this compound.

21 Claims, No Drawings

PHENOXY-PYRROLIDINE DERIVATIVE AND ITS USE AND COMPOSITIONS

RELATED APPLICATIONS

This application is the U.S. National Stage of International Application No. PCT/IB2008/002028, filed Jul. 28, 2008, published in English, and claims the benefit of U.S. Provisional Application No. 60/954,593, filed Aug. 8, 2007, the entire teachings of these applications are incorporated herein by reference.

FIELD OF INVENTION

The present invention relates to phenoxy-pyrrolidine derivatives and compositions and uses thereof, in particular phenoxy-pyrrolidine derivatives for use as stearoyl-CoA desaturase (SCD1) inhibitors.

BACKGROUND

Stearoyl-CoA desaturase (SCD1) is a microsomal, enzyme that catalyzes the de novo biosynthesis of monounsaturated fatty acids from saturated fatty acyl-CoA substrates in mammals. Specifically, SCD1 introduces a cis-double bond in the C9-C10 position of saturated fatty acids such as palmitoyl-CoA (16:0) and stearolyl-CoA (18:0). The resulting monounsaturated fatty acids, palmitoleoyl-CoA (16:1) and oleoyl-CoA (18:1), are in turn substrates for incorporation into a variety of lipids, such as phospholipids, cholesterol esters, and triglycerides. Monounsaturated fatty acids are also mediators of several other processes such as signal transduction and cellular differentiation. Lipid composition is of considerable physiologic importance. As the key component of cellular membranes, phospholipid composition ultimately determines membrane fluidity, while the composition of cholesterol esters and triglycerides may impact lipoprotein metabolism and adiposity. Studies in mice further suggest that SCD1 activity is important to maintaining the normal functioning of the skin and eyelid as a result of its major role in lipid synthesis within sebaceous and meibomian glands. Miyazaki, *J. Nutr.,* 131:2260-2268 (2001). SCD1 expression has been confirmed in the sebaceous glands of human scalp skin by immunohistochemistry and in the immortalized sebaceous gland cell line SZ95 by RT-PCR.

Skin is a lipid rich organ composed of three primary layers: the stratum corneum, the epidermis, and the dermis. The stratum corneum is the outer layer and its primary function is to serve as a barrier to the external environment. To decrease the stratum corneum's permeability to water and to keep the skin from cracking, sebaceous glands secrete an oily substance called sebum which is distributed onto the skin surface. Sebum is also secreted by the meibomian glands (or tarsal glands), a special kind of sebaceous gland located along the rim of the eyelids, to prevent evaporation of the eye's tear film. Sebum is a complex lipid mixture generally comprising free fatty acids, triglycerides, sterol esters, wax esters and squalene; however, its exact composition varies from species to species. Sebum is produced in the acinar cells of the sebaceous glands and accumulates as these cells age. Upon reaching maturation, the acinar cells lyse releasing sebum into the lumenal duct so that it may be deposited on the surface of the skin.

In humans, sebaceous glands are present in all areas of the skin except for the palms of the hands and soles of the feet. The highest concentration of these glands occurs on the scalp and face. Despite the important functions that sebum plays, many individuals experience excess sebum production which is associated with increased incidence of dermatological conditions such as acne or seborrheic dermatitis. Even in individuals without acne, excess sebum production detracts from the cosmetic appearance of the skin and hair by causing the skin to look shiny, greasy or oily and hair to look limp and dirty. Decreasing the production of sebum will alleviate oily skin and hair in individuals experiencing these conditions.

Current treatments for addressing the production of excess sebum are less than optimal. Isotretinoin, a non aromatic retinoid, has been shown to suppress sebum production by up to 90% but it is also associated with severe birth defects and a number of other potentially serious side effects. Thus, isotretinoin is only utilized for the treatment of severe acne and not simply for the reduction of sebum secretion for cosmetic purposes. Other aromatic retinoids, such as etretinate, are used in the treatment of acne but do not reduce sebum synthesis. Christos C. Zouboulis, *J. Clin. Derm.,* 22: 360-366 (2004).

Consequently, the most practical means of alleviating excess sebum production is frequent washing of the skin's surface. While frequent washing removes excess sebum from the skin, this effect is temporary and does nothing to decrease sebum production. In fact, over-washing or washing with harsh products can dehydrate the skin and actually stimulate the sebaceous glands to increase, as opposed to decrease, sebum production.

SUMMARY

The present invention provides a stearoyl CoA desaturase inhibitor, as represented by Formula I, and salts, solvates, and hydrates, thereof. The compound may also be referred to as (S)-2-(4-(hydroxymethyl)phenoxy)-1-(3-(2-(trifluoromethyl)phenoxy)pyrrolidin-1-yl)ethanone.

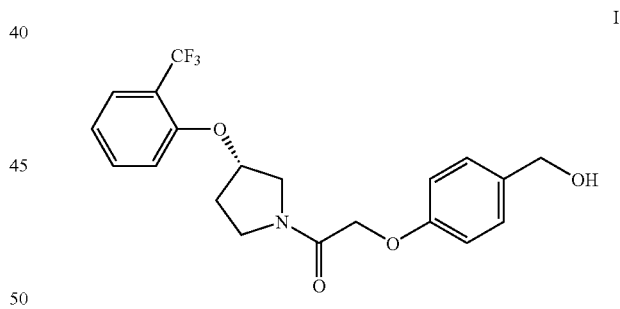

I

In another aspect, the present invention provides pharmaceutical compositions comprising a therapeutically effect amount of the compound of Formula I, or a pharmaceutically acceptable salt thereof, or a solvate or hydrate of said compound or salt and a pharmaceutically acceptable carrier, vehicle, diluent or excipient.

In another aspect, the present invention provides a method for treating a dermatologic or cosmetic condition mediated by stearoyl CoA desaturase in a mammal comprising administering to said mammal in need of such treatment a therapeutically effective amount of the compound of Formula I, or a pharmaceutically acceptable salt thereof, or a hydrate or solvate of said compound or salt. According to some embodiments, the compound of Formula I, or a pharmaceutically acceptable salt thereof, or a hydrate or solvate of said compound or salt, is administered topically in the treatment, alleviation, or prevention of excess sebum production, oily skin, oily hair, and acne. In other embodiments, the compound is administered orally.

Other aspects of the invention provide an article of manufacture or kit containing a therapeutically effective amount of compound of Formula I, or a pharmaceutically acceptable salt thereof, or a solvate or hydrate of said compound or salt, packaged for retail distribution, in association with instructions advising the consumer on how to use the compound to alleviate a condition associated with excess sebum production and/or secretion.

The compound of Formula I and pharmaceutical compositions thereof are useful for the treatment of dermatologic or cosmetic conditions mediated by stearoyl CoA desaturase. Such dermatologic or cosmetic conditions include, but are not limited to excess sebum production, acne, oily skin, oily hair, shiny or greasy-looking skin, and seborrheic dermatitis.

The compound of Formula I and pharmaceutical compositions thereof are also useful for decreasing the amount of sebum produced and/or secreted by the sebaceous glands of a human subject.

DETAILED DESCRIPTION OF THE INVENTION

The following provides additional non-limiting details of the compound of Formula I and other aspects of the invention. The headings within this document are only being utilized to expedite its review by the reader and should not be construed as limiting the invention or claims in any manner.

Definitions

As used throughout this application, including the claims, the following terms have the meanings defined below, unless specifically indicated otherwise.

The phrases "compound of Formula I", "compound of the invention", and "compound" are used interchangeably throughout the application and should be treated as synonyms.

Unless expressly stated otherwise, the phrases "compound of Formula I", "compound of the invention", and "compound" refer to (S)-2-(4-(hydroxymethyl)phenoxy)-1-(3-(2-(trifluoromethyl)phenoxy)pyrrolidin-1-yl)ethanone as well as all pharmaceutically acceptable salts, solvates, hydrates and prodrugs thereof.

The phrase "pharmaceutically acceptable" indicates that the designated carrier, vehicle, diluent, excipient, solvate, salt or prodrug is generally chemically and/or physically compatible with the other ingredients comprising a formulation, and is physiologically compatible with the recipient thereof.

The terms "treat(s)", "treating", "treated", and "treatment" as used herein include preventative (e.g., prophylactic), ameliorative, palliative and curative uses and/or results. The terms preventative or prophylactic are used interchangeably and refer to treatment prior to the onset of one or more symptoms of a particular condition or disease state. More specifically, these terms refer to the treatment of patients that are asymptomatic, i.e. where symptoms of a particular condition or disease state are not readily apparent or detectable, and which results in the substantial prevention, suppression or delay in the onset of one or more symptoms of a particular condition or disease state. An ameliorative treatment is one that improves and/or lessens the severity of one or more symptoms of a particular condition or disease state. Antibiotics such as tetracycline are an example of a preventative treatment for acne. Tetracycline prevents future outbreaks by killing the bacteria responsible for acne outbreaks.

The phrases "therapeutic" and "therapeutically effective amount" as used herein respectively denote an effect and an amount of a compound, composition or medicament that (a) treats a particular disease, condition or disorder; (b) attenuates, ameliorates or eliminates one or more symptoms of or complications arising from a particular disease, condition or disorder; (c) prevents or delays the onset of one or more symptoms of or complications associated with a particular disease, condition or disorder. It should be understood that the terms "therapeutic" and "therapeutically effective amount" encompass any one of the aforementioned effects (a)-(c), either alone or in combination with any of the others (a)-(c).

The terms "mammal", "patient" and "subject" refer to warm blooded animals such as, for example, guinea pigs, mice, rats, gerbils, cats, rabbits, dogs, monkeys, chimpanzees, and humans.

The compound of Formula I has an asymmetric center and therefore can exist in different stereoisomeric configurations. Consequently, the compound of Formula I can occur as an individual (pure) enantiomer as well as a mixture of enantiomers. The scope of the present invention includes both single enantiomers and mixtures thereof in all ratios. The scope of the present invention further includes all tautomeric forms ("tautomers") of the compound of Formula I, and all mixtures thereof in any ratio. It will be appreciated by one skilled in the art that a single compound may exhibit more than one type of isomerism.

The compound of Formula I may be resolved into the pure enantiomers by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers may be synthesized by using an optically active starting material, by asymmetric synthesis using optically active reagents, substrates, catalysts or solvents, or by converting one stereoisomer into the other by asymmetric transformation or inversion.

The compound of the present invention may exist in unsolvated as well as a variety of solvated forms with pharmaceutically acceptable solvents such as water, ethanol, and the like. In general, the solvated forms are considered equivalent to the unsolvated forms for the purposes of the present invention. It should be understood that pharmaceutically acceptable solvents further includes isotopically substituted solvents such as $D_2O$, $d_6$-DMSO and the like. The term 'solvate' is used herein to describe a complex comprising the compound of the invention and one or more pharmaceutically acceptable solvent molecules, including water. As such, all manner of hydrates of the compound are included by the term 'solvate'. It is intended that the present invention embrace unsolvated forms, solvated forms and mixtures of solvated forms in any ratio.

The compound of the present invention and/or its salts and/or solvates thereof may exist as amorphous solids or may exist in one or more crystalline states, i.e. polymorphs. Polymorphs of the compound of Formula I are encompassed in the present invention and may be prepared by crystallization under a number of different conditions such as, for example, using different solvents or different solvent mixtures; crystallization at different temperatures; and using various modes of cooling ranging from very fast to very slow during crystallization. Polymorphs may also be obtained by heating or melting a compound of Formula I followed by gradual or fast cooling. The presence of polymorphs may be determined by solid NMR spectroscopy, IR spectroscopy, differential scanning calorimetry, powder x-ray diffraction or other techniques. It should be understood that all such crystalline and amorphous forms of the compound of Formula I, and its salts, solvates and prodrugs thereof are encompassed by the invention and the claims.

The present invention also includes all pharmaceutically acceptable isotopically-labeled variations of the compound of Formula I. Such isotopically-labeled variations are compounds having the same structure and molecular formula as the compound of Formula I but wherein one or more atoms are replaced by atoms having an atomic mass or mass number different from the atomic mass or mass number usually found in nature. Examples of isotopes that may be incorporated into the compound of the present invention include isotopes of hydrogen, carbon, fluorine, nitrogen, and oxygen, such as $^2H$, $^3H$, $^{11}C$, $^{13}C$, $^{14}C$, $^{18}F$, $^{13}N$, $^{15}N$, $^{15}O$, and $^{18}O$, respectively.

Certain isotopically labeled variations of the compound of the present invention such as, for example, those incorporating a radioactive isotope such as $^3H$ and $^{14}C$, are useful in drug and/or substrate tissue distribution studies. Tritium, i.e. $^3H$, and carbon-14, i.e. $^{14}C$, are particularly preferred due their ease of preparation and detection. Further, substitution with heavier isotopes such as deuterium, i.e. $^2H$, can afford certain therapeutic advantages resulting from greater metabolic stability, for example, increased in vivo half-life or reduced dosage requirements, and hence may be preferred in some circumstances. Isotopically labeled compounds of Formula I of this invention and prodrugs thereof can generally be prepared by carrying out the procedures disclosed in the Schemes and/or in the Examples by substituting a readily available isotopically labeled reagent for a non-isotopically labeled reagent.

The compound of Formula I may be isolated and used per se or in the form of its pharmaceutically acceptable salts or solvates. The phrase "pharmaceutically acceptable salts" include pharmacologically acceptable inorganic and organic salts of said compound. These salts can be prepared in situ during the final isolation and/or purification of a compound (or prodrug), or by separately reacting the compound (or prodrug) with a suitable organic or inorganic acid and isolating the salt thus formed. A pharmaceutically acceptable salt of the compound of Formula I may be readily prepared by conventional methods such as combining the compound of Formula I and the desired acid or base, in either an aqueous, non-aqueous or partially aqueous medium, as appropriate. The resulting salt may be recovered by a number of standard methods, such as by filtration, by precipitation from solution followed by filtration, by evaporation of the solvent, or, in the case of aqueous solutions, by lyophilization. The degree of ionisation in the salt may vary from completely ionised to almost non-ionised. All such salts are within the scope of this invention.

The term "salts" is intended to refer to pharmaceutically acceptable salts and to salts suitable for use in industrial processes, such as the preparation of the compound or corresponding intermediates. These salts can exist in substantially solvated or substantially unsolvated forms or mixtures thereof. It should be understood that all such forms are within the scope of the present invention.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like. The invention further includes mixtures of different salts.

The compound of Formula I may be administered as a prodrug. The term "prodrug" refers to a compound that is transformed in vivo to yield a compound of Formula I or a pharmaceutically acceptable salt or solvate of the compound. The transformation may occur by various mechanisms, such as via hydrolysis in blood. A prodrug of the compound of Formula I may be formed in a conventional manner according to methods known in the art. A thorough discussion of prodrugs is provided in T. Higuchi and V. Stella, *Pro-drugs as Novel Delivery Systems*, Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

Synthesis

In general, the compound of Formula I may be prepared using a number of methods known in the chemical arts, particularly in light of the description contained herein, in combination with the knowledge of the skilled artisan. Various starting materials, intermediates, and reagents may be purchased from commercial sources or made according to literature methods or adaptations thereof. Although other reagents, compounds or methods can be used in practice or testing, generalized methods for the preparation of the compound of Formula I are illustrated by the following descriptions and reaction Schemes. Other processes for the preparation of the compound of Formula I are described in the experimental section. The methods disclosed herein, including those outlined in the Schemes, descriptions, and Examples are for intended for illustrative purposes and are not to be construed in any manner as limitations thereon. Various changes and modifications will be obvious to those of skill in the art given the benefit of the present disclosure and are deemed to be within the spirit and scope of the present disclosure as further defined in the appended claims.

Although specific embodiments of various aspects of the invention will be described with reference to the Schemes, Preparations and/or Examples, it should be understood that such embodiments are by way of example only and are merely illustrative of a small number of the many possible specific embodiments which can represent applications of the principles of the present disclosure.

SCHEME 1

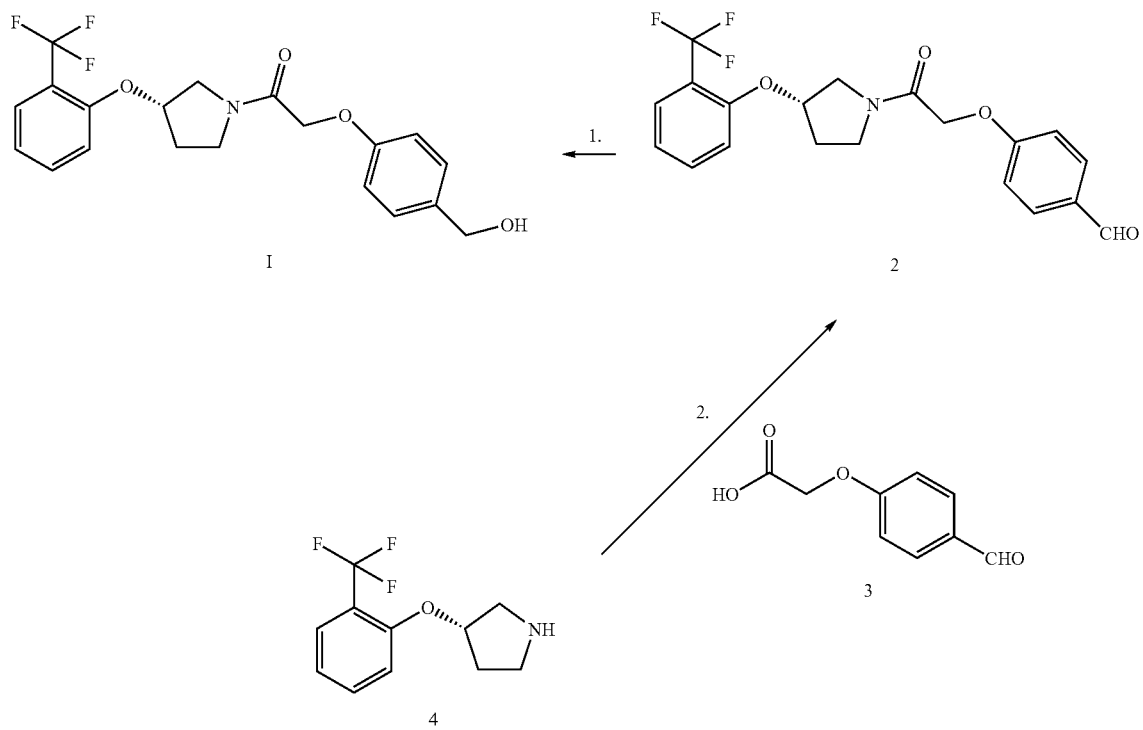

In reaction 1, the compound of Formula I may be prepared by the reduction of the corresponding aldehyde 2. The reduction is performed according to procedures known in the art. Typically, aldehyde 2 is treated with a reducing agent, such as sodium borohydride, in a polar solvent such as methanol. The mixture is allowed to stir for an appropriate time, such as between about 1 hour to about 4 hours, at a suitable temperature, such as about ambient temperature. Alternatively, aldehyde 2 may be reduced to the corresponding alcohol using hydrogen gas and an appropriate metal catalyst, such as nickel. The hydrogenation reaction is typically conducted in a polar solvent such as tetrahydrofuran (THF) at ambient temperature.

In reaction 2, aldehyde 2 may be prepared by condensing phenoxy-pyrrolidine 4 with formyl-phenoxy-acetic acid 3. The coupling reaction may be effected using diethylcyanophosphate (DECP) in the presence of an organic base, such as, for example, triethyl amine (TEA), in an aprotic solvent, such as, for example, dichloromethane. Typically, 4 and 3 are combined together with the base at a suitable temperature, such as ambient temperature. DEPC is then added dropwise to the reaction mixture. The reaction is allowed to stir for an appropriate period of time, such as between about 12 hours to about 24 hours. Alternatively, the coupling reaction may be accomplished by combining 4 and 3 in the presence of 1-hydroxybenzotriazole (HOBT), 1-ethyl-3-(3-dimethylaminopropyl)carbodiimide (EDAC) and triethyl amine (TEA), in a polar solvent or mixture of solvents, such as ethyl acetate and water, for an appropriate period of time, such as about 4 hours.

An alternate preparation of the compound of Formula I is shown below in Scheme II Scheme II

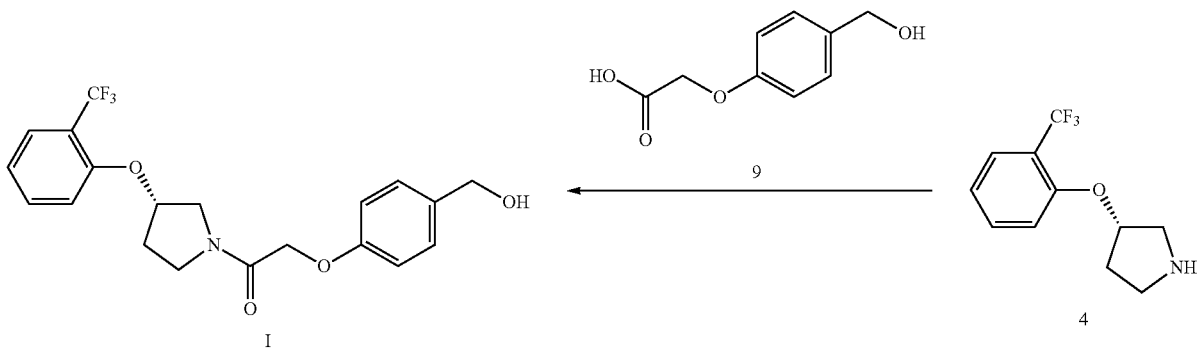

As shown in Scheme II, the compound of Formula I may be prepared by directly condensing phenoxy-pyrrolidine 4 with benzylic alcohol 9 using standard acid activation coupling procedures known in the art. Formyl-phenoxy-acetic acid 3 (Scheme I) and benzylic alcohol 9 (Scheme II) may be purchased from known commercial sources or made using procedures known in the art.

The preparation of phenoxy-pyrrolidine 4 is described in Scheme III.

In reaction 2, the N-protected phenoxy-pyrrolidine 5 may be prepared via nucleophilic substitution according to procedures known in the art. Typically, the substitution reaction is effected by combining mesylate 7 and trifluoromethyl phenol 6 together with an excess of a base, such as sodium hydride, potassium t-butoxide, potassium carbonate, cesium carbonate, etc., in an aprotic solvent such as tetrahydrofuran, N,N-dimethylformamide, etc. under an inert atmosphere (typically nitrogen) at a suitable temperature, such as about 65° C. The

SCHEME III

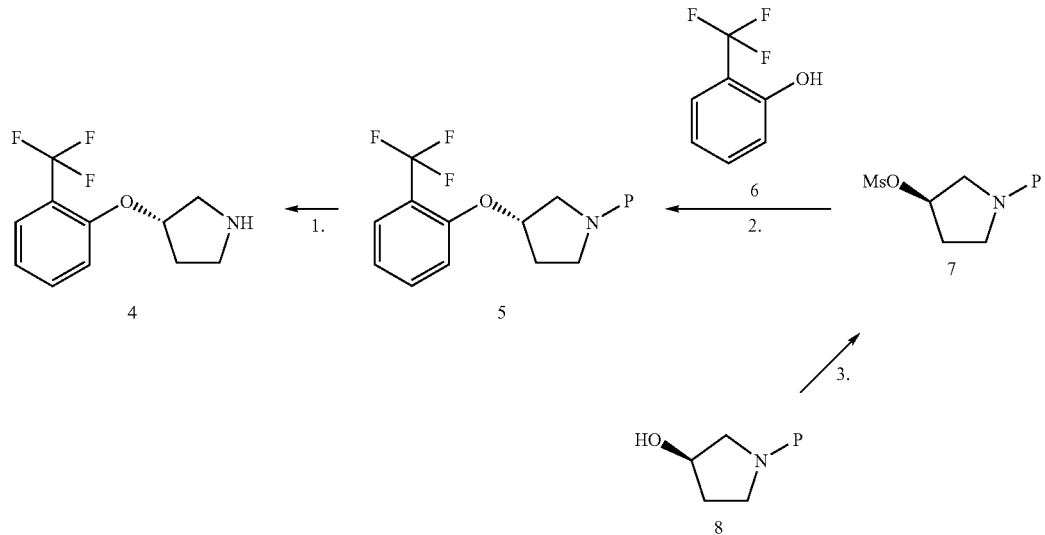

In reaction 1, phenoxy-pyrrolidine 4 may be prepared by the removal of the nitrogen protection group "P" from the corresponding N-protected phenoxy-pyrrolidine 5 according to standard deprotection procedures. For example, where P represents tert-butoxycarbonyl, the deprotection reaction can be effected using an acid such as p-toluenesolfonic acid (TsOH) or trifluoroacetic acetic acid (TFA) or an acid solution, such as HCl in dioxane. The reaction is typically conducted in a polar solvent, such as for example, diethyl ether, or solvent mixtures and is allowed to stir for an appropriate period of time such as between about 4 hours to about 24 hours at an appropriate temperature, such as for example ambient temperature. In some cases, deprotecting 5 with TFA can lead to the formation of a side product (present in about 15%) in which P represents trifluoromethylcarbonyl. Treatment of the impurity with lithium carbonate in wet ethyl acetate yields the phenoxy-pyrrolidine 4.

reaction is allowed to stir for an appropriate period of time, such as between about 4 hours to about 24 hours. Trifluoromethyl phenol 6 is known in the art and may be purchased from known commercial sources.

In reaction 3, mesylate 7 may be prepared from the corresponding N-protected hydroxy-pyrrolidine 8 according to standard procedures such as using mesyl chloride (methane sulfonyl chloride) in the presence of a base such as triethyl amine. The N-protected pyrrolidine 8, where P represents the nitrogen protecting group tert-butoxycarbonyl (BOC), is known in the art and may be purchased from known commercial sources. Alternatively, the N-protected pyrrolidine 8 may be prepared from 3-hydroxy pyrrolidine using standard procedures known in the art.

The reaction sequences described above can also be performed using a racemic N-protected pyrrolidine as the starting material as shown in Scheme IV.

Scheme IV

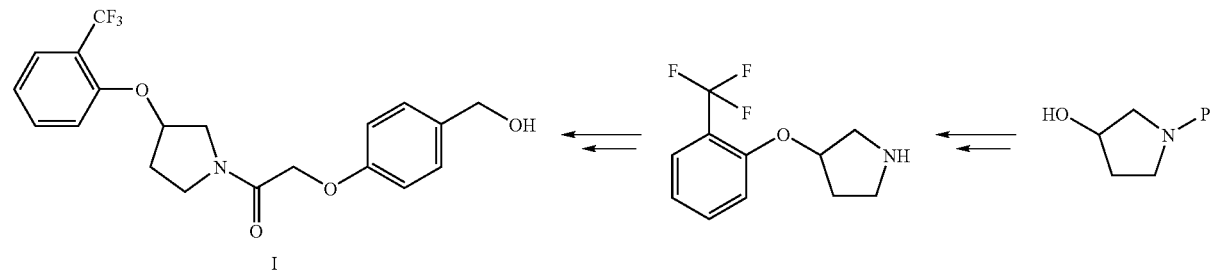

The racemic starting material corresponding to N-protected pyrrolidine 8, where P represents a nitrogen protecting group such as BOC; may also be purchased by known commercial sources.

The intermediate products described above can be recovered by extraction, evaporation, or other techniques known in the art. The crude materials may then be optionally purified by chromatography, HPLC, recrystallization, trituration, distillation, or other techniques known in the art.

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. Methods of introducing and removing protecting groups are well known to those of ordinary skill in the art and are described in Greene and Wutz, *Protective Groups in Organic Synthesis*, (3rd Ed, John Wiley & Sons, 1999).

Similarly, it would be appreciated by those skilled in the art that the standard procedures referred to in Schemes I through IV above are those that may be found in standard reference books such as e.g., the series entitled, *Compendium of Organic Synthetic Methods*, (Wiley-Interscience) and *Comprehensive Organic Transformations* by Richard Larock. Alternate reagents, starting materials, as well as methods for optimizing or adapting the procedures described herein would also be readily determined by one skilled in the art.

Medical and Cosmetic Uses

The compound of Formula I has been found to be an inhibitor of stearoyl CoA desaturase and may be useful in the treatment and alleviation of dermatologic and cosmetic conditions associated with excess sebum production and secretion. More specifically, the compound of Formula I may be used to treat, alleviate, and prevent dermatologic and cosmetic conditions such as acne, oily skin, oily hair, shiny or greasy-looking skin, and seborrheic dermatitis. As a key enzymatic regulator of lipogenesis, perturbation of SCD1 activity is believed to play a role in a wide range of diseases, such as obesity, atherosclerosis, cancer, and diabetes. For example, the targeted deletion of the SCD1 gene in mice has illustrated the importance of SCD1 to lipid homeostasis and body weight regulation. Ntambi, J. M. and Miyazaki, M., *Curr. Opin. Lipidol.* 14, 255-261 (2003) and Dobryzn A., Ntambi, J. M., *Obes. Rev.,* 6, 156-174 (2005). Other studies of SCD1 knockout mice have correlated SCD1 deficiencies with increased energy expenditure, reduced body adiposity, increased insulin sensitivity and resistance to diet-induced obesity. Dobrzyn, A., Ntambi, J. M., *Trends Cardiovasc. Med.,* 14, 77-81 (2004). Other studies have shown a positive correlation between SCD1 activity and plasma triglycerides in humans with hypertriglyceridemia. Attie, A. D. et al. *J. Lipid Res.,* 43, 1899-1907 (2002). Other studies suggest that elevated SCD1 expression and activity contributes to abnormal fatty acid partitioning in the skeletal muscle of severely obese people. Hulver, M. W. et al., *Cell Metab.,* 2, 251-261 (2005).

The link between inhibition of SCD1 and reduced sebum production has also been demonstrated in studies involving SCD1-knockout mice and mice lacking functional SCD1 as a result of a spontaneous mutation (asebia mouse). The asebia mouse is characterized as having rudimentary sebaceous glands, scaling of the epidermis and thin hair. Zheng, Y. et al, *Nature Genetics,* 23:268-270 (1999). In addition to the characteristics of asebia mouse, the SCD1-knockout mice also displayed sebocyte atrophy, the loss or reduction of sebum production and dry eyes. Miyazaki, M. et al *Journal of Nutrition,* 131(9): 2260-2268 (2001). More importantly, it was noted that the knockout mice were deficient in trigylercides and cholesterol esters, two key components of sebum, and that these deficiencies were not corrected by feeding the mice high oleate and/or palmitoleate diets. In humans, increased levels of sebum production and secretion promote the growth of *Propionibacterium acnes* which in turn contributes to inflammation, keratinocyte proliferation and lesion formation that characterize acne. Sidiropoulos M., *University of Toronto Medical Journal,* 83(2), 93-95 (2006). Therefore, inhibiting SCD1 activity so as to decrease or suppress the synthesis of sebum in the sebaceous gland should have the desired therapeutic effect in subjects afflicted with conditions associated with excess sebum production such as acne, oily skin, oily hair, shiny or greasy-looking skin, and seborrheic dermatitis.

Formulations

The compound of the present invention is intended for pharmaceutical, dermatological and cosmetic use and may be formulated as a pharmaceutical composition and administered to a mammal, such as a human patient in a variety of forms adapted to a chosen route of administration, i.e. orally, topically or subcutaneously. It should be understood that the invention is not limited by the chosen route of administration. The compound may be administered alone or in combination with one or more other therapeutic agents.

If desired, the compound can be administered directly without any excipients. However, in a typical embodiment the compound of the invention will be administered as a formulation in association with one or more pharmaceutically acceptable excipients. The term "excipient" as used herein refers to any ingredient in a formulation other than the compound of the invention such as vehicles, carriers, diluents, preservatives and the like. As used herein, the term excipient is used interchangeably with the terms "vehicle" and "carrier". The choice of excipient(s) will largely depend on factors such as the particular mode of administration, the effect of the excipient(s) on solubility and stability, and the nature of the dosage form. As used herein, the terms "formulation" and "composition" are used interchangeably. According to some embodiments, the compound will be formulated with a dermatological or cosmetic excipient. In this application the terms "dermatological excipient" and "cosmetic excipient" are used interchangeably and generally refer to ingredients or formulations suitable for administration directly to the skin or hair.

In a typical embodiment, the compound is administered topically. Topical administration is especially appropriate for the treatment of acne, excess sebum, oily skin or hair, and shiny or greasy looking skin. As used herein, topical refers to application of the compounds (and optional carrier) directly to the skin and/or hair. The topical composition according to the present invention can be in the form of solutions, lotions, salves, creams, ointments, liposomes, sprays, gels, foams, roller sticks, or any other formulation routinely used in dermatology.

In another typical embodiment, the compound is administered orally. For oral administration, the compound can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In some embodiments, the compound of Formula I is tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

In another embodiment, the compound is administered parenterally. For parenteral administration, the compound may be administered as either a solution or a suspension. Examples of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compound is being administered intrathecally, it may also be dissolved in cerebrospinal fluid as is known in the art.

In other embodiments, compositions of the invention can also comprise solid or semi-solid formulations which are suitable for use as cleansing soaps, gels or bars. These compositions are prepared according to the usual methods and may optionally contain additional excipients such as moisturizers, colorants, fragrances and the like.

The compound can also be formulated for application to the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the excipients in the various compositions according to the invention are those conventionally used in the fields considered.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

Dosage

The dose and dosing regimens of the compound of the invention may be adjusted to provide the optimum desired response in accordance with methods and practices well-known in the therapeutic arts. For example, a single bolus dose may be administered or several divided doses may be administered over time. The dose may also be proportionally reduced or increased as indicated by the exigencies of the therapeutic situation. The appropriate dosing regimen, the amount of each dose administered and/or the intervals between doses will depend upon a number of factors, including: the compound, the type of pharmaceutical composition, the characteristics of the subject in need of treatment and the severity of the condition being treated.

The dose of the compound will vary, but as a general guideline for dermatological administration, the compound will be present in a dermatologically acceptable formulation in an amount of from about 0.01 to 50 w/w %, and more typically from about 0.1 to 10 w/w %. In some embodiments, the formulation may be applied to the affected area from 1 to 4 times daily. A "dermatologically acceptable formulation" is one that may be applied to the skin or hair and will allow the drug to diffuse to the site of action.

The dose of the compound will vary, but as a general guideline for oral dosing, the compound will be present in a formulation suitable for oral administration in an amount from about 0.1 mg to about 1.0 grams. In some embodiments, the compound will be orally administered once a day. In other embodiments, the compound will be orally administered more than once a day. As used herein the phrase "oral administration" means taken by mouth.

The skilled artisan can also be expected to readily determine the maximum tolerable dose, the therapeutically effective amount which provides a detectable therapeutic benefit to a patient, and the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention. The determination of optimal dosages for a particular patient is well-known to those skilled in the art.

Certain non-limiting examples of pharmaceutically acceptable vehicles suitable for topical administration include propylene glycol:transcutanol:ethanol (20:20:60, v/v/v) and propylene glycol:ethanol (30:70, v/v). In some embodiments, the compound of Formula I may be present at concentrations of between about 1.5% to about 2.0% (w/v).

Co-Administration

In further embodiments of the invention, the compound is co-administered with other agents in order to enhance or complement the desired therapeutic effect or to minimize potential side effects. Non-limiting examples of such embodiments are described below.

Acyl CoA cholesterol acyl transferase (ACAT) inhibitors were initially evaluated for the treatment of elevated serum cholesterol. It was subsequently discovered that these compounds decrease sebum production (U.S. Pat. No. 6,133,326). Any such ACAT inhibitor can be co-administered with the compound of Formula I to decrease sebum production, alleviate oily skin, etc.

Antibiotics, such as tetracycline and clindamycin, have been used to alleviate acne. The antibiotic eradicates the microorganism, *Propionbacterium acnes*, leading to a reduction in the patient's acne. The compound of Formula I can be co-administered with any antibiotic suitable for the treatment of acne.

Certain retinoids are used to treat acne but do not effectively reduce sebum production. In an embodiment of the invention, the compound of Formula I is co-administered with a retinoid in order to decrease sebum production and to treat acne or seborrhoea. Exemplary retinoids suitable for co-administration include, but are not limited to, etretinate, tretinoin, and aliretinoin.

Estrogen and progesterone have each been shown to decrease sebum production. These compounds, or any synthetic agonist of such compounds, may be co-administered with the compound of formula I in order to decrease sebum production.

As used in this application, the terms "co-administered" or "co-administration" refer to a dosing regimen where the compound of Formula I is administered with a second therapeutic agent, typically having a differing mechanism of action, to promote a desired result. It should be understood that "co-administration" is not limited by the route(s) of administration and can refer to simultaneous dosing, dosing at different times during a single day, or even dosing on different days. The compounds can be administered separately or can be combined into a single formulation (i.e. fixed combination).

In another embodiment, the medicinal and cosmetic formulations containing the compound and any additional therapeutic agents will typically be packaged for retail distribution (i.e. an article of manufacture or a kit). Such articles will be labeled and packaged in a manner to instruct the patient how to use the product. Such instructions will include the condition to be treated, duration of treatment, dosing schedule, etc.

The compound of Formula I may also be admixed with any inert carrier and utilized in laboratory assays in order to determine the concentration of the compounds within the serum, urine, etc., of the patient as is known in the art. The compound may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data are being presented in order to further illustrate the invention. This disclosure should not be construed as limiting the invention in any manner.

In the discussions below, the following abbreviations were used: THF (tetrahydrofuran), DMF (N,N-dimethylformamide), BOC (tert-butoxycarbonyl), DEPC (diethylcyanophosphate), TEA (triethyl amine), HOBT (1-hydroxybenzotriazole), EDAC (1-ethyl-3-(3-dimethylaminopropyl) carbodiimide), and EtOH (ethanol),

EXAMPLES

Example 1A (S)-2-(4-(hydroxymethyl)phenoxy)-1-(3-(2-(trifluoromethyl)phenoxy)pyrrolidin-1-yl)ethanone Step 1: A mixture of R-1-BOC-3-hydroxy-pyrrolidine (1.0 g, 5.34 mmol) and triethylamine (0.89 ml, 6.41 mmol) in THF (20 ml) was cooled in an ice bath. To this was added methane sulfonyl chloride (0.46 ml, 5.87 mmol). The reaction was then warmed to ambient temperature and allowed to stir for 4 hours. The reaction was quenched with the addition of water, and extracted with ethyl acetate (2×). The organic extracts were combined, washed with saturated NaCl solution, dried over anhydrous MgSO$_4$, filtered and concentrated to provide 1.42 g of a clear oil which was used without further purification.

$^1$H NMR δ (ppm) (CDCl$_3$) 1.48 (9 H, s), 2.05-2.30 (2 H, m), 3.05 (3 H, s), 3.40-3.75 (4 H, m), 5.27 (1 H, br).

Step 2: The product of Step 1 was combined with 2-(trifluoromethyl)phenol (868 mg, 5.35 mmol) and cesium carbonate (2.620 g, 8.03 mmol) in DMF (15 ml). The resulting mixture was warmed to 65° C. and allowed to stir overnight. Water was added and the reaction was extracted with ethyl acetate (2×). The organic extracts were combined, dried over MgSO$_4$, filtered and concentrated to provide 1.77 g of a yellow oil which was used without further purification.

$^1$H NMR δ (ppm) (CDCl$_3$) 1.50 (9 H, s), 2.02-2.30 (2 H, m), 3.40-3.70 (4 H, m), 5.01 (1 H, br.), 6.90-7.10 (2 H, m), 7.40-7.70 (2 H, m)

MS (M+1-100)=232 .

Step 3: The product of Step 2 (1.77 g, 5.15 mmol) was dissolved in diethyl ether (20 ml). To this was added 4 M HCl in dioxane (5.0 ml) and the reaction mixture was allowed to stir overnight. The resulting precipitate was collected by filtration and washed with diethyl ether to provide 0.86 g of a white solid that was used with further purification.

$^1$H NMR δ (ppm) (CDCl$_3$) 2.30-2.42 (2 H, br.), 3.40-4.20 (4 H, m), 5.18 (1H, br.), 6.90-7.10 (2 H, m), 7.40-7.60 (2 H, m).

MS (M+1)=232

Step 4: The product of Step 3 (2.00 g, 8.65 mmol) was combined with 2-(4-formylphenoxy)acetic acid (1.42 g, 7.86 mmol) and triethyl amine (2.85 ml, 20.4 mmol) in dichloromethane (40 ml). To this was added DEPC (1.55 ml, 10.2 mmol) dropwise over five minutes. The reaction mixture was then allowed to stir for eighteen hours at ambient temperature. The reaction was concentrated to 50% volume and purified via medium pressure liquid chromatography using a 5%-100% ethyl acetate/hexanes elution gradient to provide 1.83 g of a clear colorless oil.

$^1$H NMR δ (ppm)) (CDCl$_3$) 2.41-2.08 (2 H, m), 3.69-3.94 (4 H, m), 4.61-4.66 (2 H, m), 5.06 (1 H, m), 6.89-7.58 (m, 7H), 9.90 (1 H, s).

MS (M+1)=394

Step 5: The product of Step 4 (1.83 g, 4.65 mmol) was dissolved in methanol (25 ml). To this was added sodium borohydride (968 mg, 2.56 mmol). The resulting mixture stirred for 2 hours at ambient temperature whereupon 5.0 ml of 2N NaOH was added and the reaction stirred for an additional 1 hour. The reaction was then diluted with 100 ml of ethyl acetate, 20 ml of saturated NaCl solution and stirred for 5 minutes. The organic layer was separated and the aqueous layer was washed with ethyl acetate (2×, 30 ml). The organic layers were combined, dried over anhydrous sodium sulfate, filtered and concentrated. The crude material thus obtained was purified via medium pressure liquid chromatography to provide a pale yellow gum which was dissolved in 10 ml of dichloromethane and triturated with heptane to provide the title compound as a white solid. This solid was collected via filtration and dried at 50 C for 18 hours.

$^1$H NMR δ (ppm) (CDCl$_3$) 1.64 (1 H, s), 2.41-2.08 (2 H, m), 3.69-3.94 (4 H, m), 4.61-4.66 (4H, m), 5.06 (1 H, m), 6.89-7.58 (m, 7H).

MS (M+1)=396

$[α]^{20}_D$=122.3 (c 5.3, MeOH)

Chiral HPLC: retention time: 12.62 min (condition: column-chiralcel OJ, #0500CE-KJ010, 4.6×250 mm, solvent: EtOH/Heptane 25/75, flow rate: 0.9 ml/min).

Example 1B

This example illustrates an alternative preparation of the compound of the invention.

Step 1: (S)-3-(2-(trifluoromethyl)phenoxy)pyrrolidine (200 g, 0.579 mol) containing ca. 15% of (S)-2,2,2-trifluoro-1-(3-(2-(trifluoromethyl)phenoxy)pyrrolidin-1-yl)ethanone was combined with Li$_2$CO$_3$ (85.61 g, 1.16 mol) in ethyl acetate (500 ml) and water (100 ml). The resulting reaction mixture was stirred for 2 hours then partitioned between water and ethyl acetate. The organic layer was separated and washed with water (2×) and used in the next step without concentrating or isolating the product.

Step 2: The organic product layer from Step 1 was treated with (4-formylphenoxy)acetic acid (95.0 g, 0.527 mol) in the presence of HOBT (71.17 g, 0.527 mol) and EDAC (131.24 g, 0.685 mol). To the resulting slurry was added TEA (100 ml, 0.717 mol) and water (50 ml) whereupon the reaction exothermed to 37 C. The mixture was then stirred at ambient temperature for 3 hours after which the reaction was portioned with water. The organic layer was then washed as follows: water (1×), aqueous 1.0 M HCl (1×), saturated aqueous NaHCO$_3$ (1×), aqueous 1.0 M HCl (1×), and saturated aqueous NaHCO$_3$ (1×). Silica gel (150 g) was then added to the organics and the mixture stirred for 5-10 minutes before filtering. The organics were then used in the next reaction step without concentrating or isolating the product.

Step 3: The ethyl acetate solution of the product from Step 2 was added to a SS Parr shaker with an operating volume of 1600 ml. To this was added nickel (100 g) which was washed with methanol and THF to remove water prior to addition. The resulting reaction mixture was purged with nitrogen (3×) then purged with hydrogen (5×) then pressurized to 50 psi with hydrogen gas. The mixture was shaken at ambient temperature under 50 psi taking care not to let the reaction temperature to exceed 45° C. Reaction was monitored for uptake of hydrogen, repressurizing reaction vessel as necessary. Once H$_2$ uptake stopped, the reaction was filtered to remove nickel. Nickel was then washed with THF to dissolve any product that precipitated. Organics were combined and filtered through a pad of celite before concentrating to approximately 400 ml. To this was added hepanes (approx. 650 ml) and the mixture stirred until product precipitates. Solids were then collected via filtration and washed with ethyl acetate to provide crude product (171 g). The material thus obtained were then combined with 800 ml of ethyl acetate and heated to 80° C. until all solids dissolved. The solution is then stirred at ambient temperature until product crystallizes. When the solution reaches about 30° C. the solids are filtered and washed with ethyl acetate and dried under vacuum at 50° C. for 16 hours to provide (S)-2-(4-(hydroxymethyl)phenoxy)-1-(3-(2-(trifluoromethyl)phenoxy)pyrrolidin-1-yl)ethanone.

Example 1C

This example illustrates the preparation of the opposite enantiomer of the compound of the invention, namely, (R)-2-(4-(hydroxymethyl)phenoxy)-1-(3-(2-(trifluoromethyl)phenoxy)pyrrolidin-1-yl)ethanone.

A mixture of the product of Step 3 (700 mg, 2.62 mmol) in Example 1A, 2-(4-hydroxymethyl)phenoxy)acetic acid (855 mg, 4.7 mmol), HOBT (376 mg, 2.78 mmol), EDAC.HCl (621 mg, 3.24 mmol), and 4-methylmorpholine (3 g, 30 mmol) in methylene chloride (20 mL) was stirred for 18 hours at 23 C. The reaction mixture was diluted with methylene (20 mL) and washed with water (30 mL) as well as 5% citric acid solution (30 mL). The organic layer was dried over MgSO$_4$, filtered, and concentrated. Further recrystallization from ethyl acetate/heptane provided the desired product (Example 1C, 645 mg, 76.1% in yield).

$^1$H NMR δ (ppm) (CDCl$_3$) 1.58 (1 H, s) 2.43-2.08 (2 H, m), 3.6-3.94 (4 H, m), 4.61-4.66 (4H, m), 5.06 (1 H, m), 6.89-7.58 (m, 7H).

MS (M+1)=396

Chiral HPLC: retention time: 15.17 min (conditions: column-chiralcel OJ, #0500CE-KJ010, 4.6×250 mm, solvent: EtOH/Heptane 25/75, flow rate: 0.9 ml/min).

Pharmacological Testing

Rat Microsomal Assay

The following rat microsomal assay was used to demonstrate the inhibitory activity of the compound of Formula I against stearoyl CoA desaturase (SCD1). As described below, the assay measures the conversion of labeled stearoyl CoA to oleoyl CoA using LC/MS/MS.

In order to increase SCD1 activity in rat liver microsomes, Sprague Dawley rats are fasted for 40 hours. Following fasting diet is replaced with free fatty acid deficient chow ad libitum for 48 hours. Rats are then euthanized using CO$_2$ asphyxiation and their livers are removed. Livers are weighed, minced and placed in homogenization buffer (0.15 mM KCl, 0.25 mM sucrose, 50 mM Tris-HCl, pH 7.5, 5 mM EDTA, 1.5 mM GSH) on ice. Microsomes are isolated by homogenization with a polytron and several centrifugation steps. Following final centrifugation, the resulting pellet is resuspended in homogenization buffer and protein concentration is determined. Aliquots are stored at −80° C. until use.

Rat liver microsomes are allowed to react with stearoyl-coenzyme A labeled with D3 in the presence of the compound of Formula I to test the compound's ability to inhibit the conversion of stearoyl-coenzyme A to oleoyl coenzyme A. The reaction is terminated using acetonitrile. Free fatty acids are extracted by saponification of the samples with 2M KOH at 70° C. Samples are then acidified with formic acid and finally extracted with chloroform. The organic layer is transferred and evaporated under nitrogen gas. Samples are reconstituted in 9:1 Methanol:Water, with 2 ug/ml heptadecanoic acid added as an internal standard, and analyzed by LC/MS/MS. The ability to inhibit the conversion of stearoyl CoA to oleoyl CoA is expressed as an IC$_{50}$.

Using the assay described above, the compound of Formula I inhibited SCD1 activity with an IC$_{50}$ of 5.8 nM in the presence of 40 μM substrate (2× K$_m$). This value is the mean of multiple tests (N=3).

Human Adipocyte Assay

The role of SCD1 is believed to be similar in adipocytes and sebocytes. The ability of the compound to inhibit the SCD1 enzyme in intact human cells was determined using the Human AdipoRed assay as described below. The cells were received as pre-adipocytes and then differentiated for 5 days in a 384 well format. The compound is added at various concentrations for 6 days. The production of triglycerides was then assessed by a unique dye which specifically binds to secreted triglycerides. The ability to inhibit the production of triglycerides is expressed as an IC$_{50}$.

Experimental Procedure for Human Adipocyte Assay

Cryopreserved subcutaneous preadipocytes (Cat #: PT-5001 Supplier: Cambrex Bio Science) were briefly thawed in 37 C and spin down at 1000 rpm for 5 minutes. Preadipocyte are resuspended in 30 ml of Growth Media (GM, Cat #: PT-8202 Cambrex Bio Science) and are diluted to final concentration of 75,000 cells/ml. 40 ul of Cells are then plated into wells of 384-Well BD Falcon polystyrene assay plate at the density of 3,000 cells (40 μl) per well.

After 3 days, cells are induced into differentiation by adding 40 μl of 2× Differentiation Media (DM, Cat #: PT-9502 Cambrex Bio Science) into each well.

After 5 days' differentiation, cells were treated with 2 μl of the compound from 96-well compound plate in duplicate by Biomek FX. After 6 days compound treatment, 384-well plates containing the differentiated adipocyte are washed with DPBS twice and stained with 1.5 μl of AdipoRed (Cat #: PT-7009 Cambrex Bio Science) reagent for 15 minutes at room temperature. The accumulation of intracellular triglycerides is then quantified by measuring fluoresce at 572 nm on a SpectraMax M5 microplate reader.

Using the assay described above the compound of the invention was determined to have an $IC_{50}$ of 6.8 nM. This value is the mean of multiple tests (N=6).

Hamster Ear Model

The hamster ear model is a validated animal model for testing whether compounds are capable of modulating sebaceous gland function and sebum secretion. Luderschmidt et al, *Arch. Derm. Res.* 258, 185-191 (1977). This model uses male Syrian hamsters, whose ears contain sebaceous glands. The compound of the invention was screened in this model according to the procedure outlined below. In these studies, the hamsters are topically dosed twice daily (BID) for 2 weeks, 5 days a week (Monday to Friday). Each dose consisted of 25 μl of vehicle control or formulated test article, which was evenly applied to ~3 $cm^2$ of the ventral surfaces of both the right and left ears. At sacrifice, skin punches are taken for lipid analysis, histology and skin concentrations of the test compound.

Animal Model for Inhibition of Sebum Production

Male Syrian hamsters aged 9 to 10 weeks were introduced into the laboratory environment and acclimated for 2 weeks prior to use in the study. Each group consisted of 5 animals and run in parallel with vehicle and positive controls. Prior to administration, a sufficient quantity each compound was dissolved in 1 mL of a solvent consisting of ethanol, transcutanol, and propylene glycol (60/20/20 v/v/v) to achieve a final concentration of 3.0 w/v %.

Animals were dosed topically twice daily, five days a week, for 2 weeks. Each dose consisted of 25 μl of vehicle control or drug. The dose was applied to the ventral surfaces of both the right and left ears. All animals were sacrificed approximately 18-24 hours after the final dose. The right ears were collected from each animal and used for sebum analysis.

The ears were prepped for HPLC analysis in the following manner. One 8 mm distal biopsy punch was taken, just above the anatomical "V" mark in the ear to normalize the sample area. The punch was pulled apart. The ventral biopsy surface (the area where the topical dose was directly applied to the sebaceous glands) was retained for testing and the dorsal surface of the biopsy punch was discarded.

Tissue samples were blown with $N_2$ gas and stored at −80° C. under nitrogen until HPLC analysis. In addition to ear samples, an aliquot of each drug and vehicle (at least 250 μl) was also stored at −80° C. for inclusion in the HPLC analysis.

HPLC analysis was carried out on an extract of the tissue sample. Tissue samples were contacted with 3 ml of solvent (a 4:1 admixture of 2,2,4-trimethylpentane and isopropyl alcohol). The mixture was shaken for 15 minutes and stored overnight at room temperature, protected from light. The next morning 1 milliliter of water was added to the sample and shaken for 15 minutes. The sample was then centrifuged at approximately 1500 rpm for 15 minutes. Two ml of the organic phase (top layer) was transferred to a glass vial, dried at 37° C., under nitrogen, for approximately 1 hour, and then lyophilized for approximately 48 hours. The samples were then removed from the lyophilizer and each vial was reconstituted with 600 μl of solvent A (trimethylpentane/tetrahydrofuran (99:1). The samples were then recapped and vortexed for 5 minutes.

200 μl of each sample was then transferred to a pre-labeled 200 μl HPLC vial with 200 μL glass inserts. The HPLC vials were placed in the autosampler tray for the Agilent 1100 series HPLC unit. The Agilent 1100 HPLC system consisted of a thermostated autosampler, a quarternary pump, a column heater, and an A/D interface module. All components were controlled by Agilent ChemStation software. A Waters Spherisorb S3W 4.6×100 mm analytical column was maintained at 30° C. by the Agilent column heater unit. The HPLC autosampler was programmed to maintain the sample temperature at 20° C. throughout the run.

10 μL of each sample was injected in triplicate into the column. Two solvents were used for the solvent gradient. Solvent A was an admixture of trimethylpentane and tetrahydrofuran (99:1). Solvent B was ethyl acetate. The gradient utilized is described in the table below:

| Time (min) | Solv A (%) | Solv B (%) | Flow (mL/min) |
|---|---|---|---|
| 0 | 99 | 1 | 2 |
| 2 | 96 | 4 | 2 |
| 6 | 60 | 40 | 2 |
| 7 | 5 | 95 | 2 |
| 10 | 5 | 95 | 2 |
| 10.1 | 99 | 1 | 2 |

The Sedex 75 Evaporative Light Scattering Detector (ELSD) was operated at 45° C. with a gain of 5, and $N_2$ pressure maintained at 3.1 bar. Analog signal obtained by the instrument was sent to the Agilent A/D interface module where it was converted to a digital output. The conversion was based on a 10000 mAU/volt set point and the data rate was set at 10 Hz (0.03 min). The resulting digital output was then feed into the Agilent ChemStation software for integration of the peak area. The results are reported as the reduction in cholesterol ester (CE) and wax ester (WE) production, when compared to the vehicle control. A negative value reflects an increase in sebum, whereas a positive reflects a decrease.

Using this assay it was determined that treatment with the test compound (dosed at 1.5% in a vehicle of propylene glycol/transcutanol/ethanol 20/20/60, w/v) resulted in a 62% reduction in CE and an 82% reduction in WE, a mechanism biomarker for sebum production in the hamster model, and a reduction in sebaceous gland size. A dose response experiment was then performed to determine the $ED_{50}$ of the compound. For this study, the test compound was formulated in propylene glycol:ethanol, 30:70, (w/v) resulted in a dose dependent decrease of both CE and WE production. Dose related changes in sebaceous gland size and number were also observed histologically. The $ED_{50}$ based on WE reduction for the compound of Formula I was determined to be 0.3% (0.025 $mg/cm^2$) for two week topical BID application.

What is claimed is:
1. The compound of Formula I

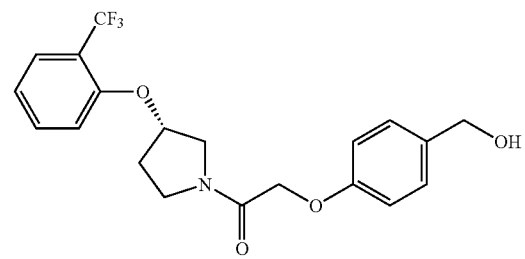

I or a pharmaceutically acceptable salt thereof.

2. A method of reducing or preventing the synthesis of sebum, comprising administering to mammal in need thereof a therapeutically effective amount of the compound of Formula I

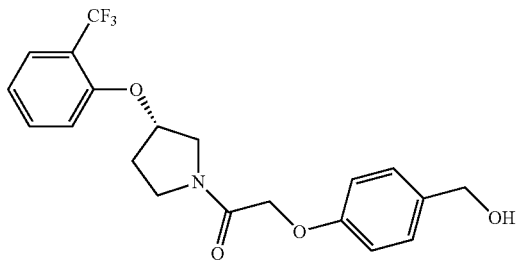

or a pharmaceutical acceptable salt thereof.

3. A method of reducing or preventing the synthesis of cholesterol esters and wax esters in the sebaceous glands of a mammal, comprising administering to a mammal in need thereof a therapeutically effective amount of the compound of Formula I

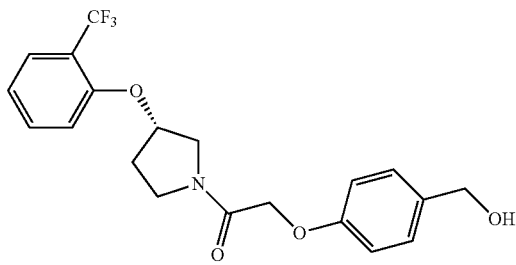

or a pharmaceutically acceptable salt thereof.

4. A method of treating acne, comprising administering to a mammal in need thereof a therapeutically effective amount of the compound of Formula I

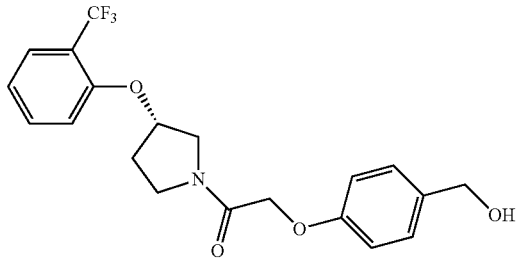

or a pharmaceutically acceptable salt thereof.

5. The compound (R)-2-(4-(hydroxymethy)phenoxy)-1-(3-(2-(trifluoromethly)phenoxy)pyrrolidin-1-yl)ethanone.

6. The compound 2-(4-hydroxymethyl)phenoxy)-1-(3-(2-trifluoromethyl)phenoxy)pyrrolidin-1-yl)ethanone.

7. A pharmaceutical composition comprising: the compound (S)-2-(4-(hydroxymethyl)phenoxy)-1-(3-(2-(trifluoromethyl)phenoxy)pyrrolidin-1-yl)ethanone, or a pharmaceutically acceptable salt of said compound; and a pharmaceutically acceptable carrier, vehicle, diluent or excipient.

8. A pharmaceutical composition comprising: the compound (S)-2-(4-(hydroxymethyl)phenoxy)-1-(3-(2-(trifluoromethyl)phenoxy)pyrrolidin-1-yl)ethanone, or a pharmaceutically acceptable salt of said compound; a second therapeutic agent; and a pharmaceutically acceptable carrier, vehicle, diluent or excipient.

9. The composition of claims 7 wherein said composition is suitable for applying to the skin or hair.

10. The composition of claims 7 wherein said composition is suitable for ingestion.

11. A method of treating or alleviating a condition associated with excess sebum production in a mammal in need of such treatment comprising administering to said mammal a therapeutically effective amount of (S)-2-(4-(hydroxymethyl)phenoxy)-1-(3(2-(trifluoromethyl)phenoxy)pyrrolidin-1-yl)ethanone, or a pharmaceutically acceptable salt of said compound, alone or in combination with a second therapeutic agent.

12. A method of treating or alleviating a condition selected front acne, oily skin, oily hair, shiny skin, greasy-looking skin, greasy-looking hair, or seborrheic dermatitis in a mammal in need of such treatment comprising administering to said mammal a therapeutically effective amount of (S)-2-4-(hydroxymethyl)phenoxy)-1-(3-(2-(trifluoromethyl)phenoxy)pyrrolidin-2-yl)ethanone, or a pharmaceutically acceptable salt of said compound, alone or in combination with a second therapeutic agent.

13. A method of reducing or preventing the activity of stearoyl CoA desaturase in a mammal in need of such treatment comprising administering to said mammal a therapeutically effective amount of (S)-2-(4-(hydroxymethyl)phenoxy)-1-(3-(2-(trifluoromethyl)phenoxy)pyrrolidin-1-yl) ethanone, or a pharmaceutically acceptable salt of said compound, alone or in combination with a second therapeutic agent.

14. A kit comprising a compound according to claim 1 packaged for retail distribution, which advises a consumer how to utilize the compound to alleviate a condition associated with excess sebum production.

15. A kit comprising a compound according to claim 1 packaged for retail distribution, which advises a consumer how to utilize the compound to alleviate a condition selected from acne, oily skin, oily hair, shiny skin, greasy-looking skin, greasy looking hair, seborrheic dermatitis.

16. The method of claim 2, wherein said mammal is a human.

17. The method of claim 3, wherein said mammal is a human.

18. The method of claim 4, wherein said mammal is a human.

19. The method of claim 11, wherein said mammal is a human.

20. The method of claim 12, wherein said mammal is a human.

21. The method of claim 13, wherein said mammal is a human.

* * * * *